United States Patent [19]

Jones

[11] Patent Number: 5,394,339

[45] Date of Patent: Feb. 28, 1995

[54] APPARATUS FOR ANALYZING OIL WELL PRODUCTION FLUID

[75] Inventor: Ray L. Jones, Placentia, Calif.

[73] Assignee: Paul-Munroe Hydraulics Inc., Orange, Calif.

[21] Appl. No.: 860,550

[22] Filed: Mar. 30, 1992

[51] Int. Cl.$^6$ .................. G01N 9/26; G01N 9/36; G01F 15/08; F17D 3/10

[52] U.S. Cl. ................... 364/510; 364/499; 73/61.44; 137/601

[58] Field of Search ............... 364/509, 510, 497, 499, 364/550; 73/61.47, 61.44, 61.76, 61.78; 137/601

[56] References Cited

U.S. PATENT DOCUMENTS

| | | | |
|---|---|---|---|
| 3,200,312 | 8/1965 | Callahan | 317/246 |
| 3,911,256 | 10/1975 | Jones | 364/510 |
| 4,869,102 | 9/1989 | Hale et al. | 73/168 |
| 4,875,623 | 10/1989 | Garris | 236/12.12 |
| 4,881,412 | 11/1989 | Northedge | 73/861.04 |
| 4,916,617 | 4/1990 | Norwood | 364/422 |
| 4,924,695 | 5/1990 | Kolpak | 73/61.1 R |
| 4,975,645 | 12/1990 | Lucas | 324/324 |
| 5,101,367 | 3/1992 | Agar | 364/551.01 |
| 5,249,455 | 10/1993 | Cox | 73/61.44 |
| 5,251,488 | 10/1993 | Naberman et al. | 73/861.04 |

Primary Examiner—Michael Zanelli
Attorney, Agent, or Firm—Georges A. Maxwell

[57] ABSTRACT

An improved apparatus and method for analyzing oil well production fluid that includes a flow pipe through which production fluid normally flows, a test pipe defining an elongate vertical test chamber, valves to selectively intermittently bypass fluid flowing through the flow pipe into the test pipe to fill the chamber with a sample of production fluid. The apparatus includes devices to measure and record the rate of flow of the production fluid flowing through the flow pipe and to measure and record the temperature, pressure, weight and the capacitance of the sample in the chamber for comparative use with earlier recorded base measurements to calculate and record the net volumes of the oil, gas and water fractions in the production fluid.

1 Claim, 1 Drawing Sheet

APPARATUS FOR ANALYZING OIL WELL PRODUCTION FLUID

BACKGROUND OF THE INVENTION

The present invention has to do with the testing and/or analyzing of fluid mixtures flowing through fluid conducting lines and is particularly concerned with an improved apparatus that is particularly suited for analyzing and determining the net volumes of oil, gas and water of production fluid flowing from oil wells.

The present invention has to do with certain notable improvements in that apparatus for testing and analyzing fluid mixtures that is the subject matter of and that is fully disclosed in my earlier issued U.S. Pat. No. 3,911,256, issued Oct. 7, 1975. The full disclosure of U.S. Pat. No. 3,911,256 is incorporated herein by reference and will hereinafter be referred to as the patent.

To the best of my knowledge and belief, the patent is the most pertinent prior art and was representative of the state of the art at the time of my present invention.

In the patent the need for determining the net oil content of the production fluids issuing from oil wells is fully and clearly set forth.

The patent also describes that old method and apparatus employed to test oil well production fluids to determine the net oil content thereof that was, and remains, the most common and widely used method and apparatus for determining the net oil content of oil well production fluid throughout the petroleum industry at the time of the invention of the patent apparatus. That old and common method and apparatus for testing production fluid is characterized by the provision and use of three-phase separator tanks in and through which production fluids issuing from oil wells are caused to flow at a sufficiently slow rate to allow the force of gravity to cause free water in the production fluid to settle to the bottoms of the tanks, for the lighter oils to rise to the top of the settled water and for free gases to rise in the tanks above the oil. The volumes of separated water, gas and oil in the tanks are measured and recorded and samples of the separated oil (wet oil) are extracted from the tanks and tested to determine the net volumes of the water, gas and oil fractions thereof.

In the apparatus of the referred-to patent, the use of a three-phase separator tank is eliminated and in its stead the apparatus includes an elongate vertical test chamber that is filled with and holds a sample of production fluid to be tested. That apparatus operates to read and record the flow rate, temperature, pressure and weight of the sample of fluid in the chamber and operates to alter the pressure on the sample in the chamber to expand or compress the gas in the chamber and to vary the volume of the sample in the course of calculating and determining the net gas content of the sample. The net oil and/or net water content of the sample is determined by subtracting the measured volume and weight of the gas from the total volume and weight of the sample to determine the net volume and weight of the remaining water and oil in the sample and comparing the measured volume and weight of the water and oil with base or reference measurements of the volume and weight earlier obtained from a prepared anhydrous sample of the oil. The net volume of oil in the sample being tested is established by subtracting the measured weight thereof from the measured weight of a like volume of anhydrous oil.

The apparatus of the referenced patent has proven to be effective to test and determine the net oil content of oil well production fluid containing oil that has a specific gravity that is notably different from the specific gravity of water. As the specific gravity of oil in production fluid tested nears the specific gravity of water, the difficulty and time required to calculate and determine the net content of oil increases at an exponential rate and the accuracy and dependability of the apparatus diminishes in a like manner. That apparatus is rendered totally ineffective when the specific gravity of the oil is the same as water. In practice, the apparatus of the referred-to patent cannot reliably and dependably analyze oil well production fluid containing oil the API gravity of which is between 14 and 7 degrees API. Accordingly, the apparatus of my referred-to patent is not suitable for use in analyzing oil well production fluids containing those heavy crude oils that characterize the production from most oil deposits throughout the world.

In addition to the foregoing, the apparatus which is the subject matter of my above referred-to patent has proven to be such that it requires closer monitoring and field service than many of those who own, maintain and service oil field production equipment are willing to be burdened with. This is due to the fact that the apparatus includes many mechanical parts that are subject to leaking and failing and that must be periodically serviced, repaired and/or replaced. For example, the patented apparatus includes the flow meter, four large fall valves, a double-acting hydraulic cylinder and piston unit and link means for operating those valves; a source of motive hydraulic fluid and an electrically operated four-way valve for controlling operation of the cylinder and piston unit; a motor-driven high-pressure liquid pump with a related check valve and an electrically operated plug valve for introducing and removing liquid from the test chamber. It is an accepted rule-of-thumb that the likelihood of mechanical failure in such apparati increases exponentially with the number of mechanical parts included.

OBJECTS AND FEATURES OF THE INVENTION

It is an object of my invention to provide an improved apparatus for testing and analyzing oil production fluid to determine the net oil content thereof that overcomes many of the shortcomings that are to be found in and that characterize apparatus provided by the prior art for analyzing such fluids to determine the net oil content thereof.

It is an object and a feature of my invention to provide a novel and improved apparatus for the purpose set forth above which is such that the gas, water and oil fractions or components of a sample of production fluid being analyzed are not and need not be separated or otherwise worked upon in the course of analyzing and determining the net content of the oil, gas and/or water thereof.

Yet another object and feature of my invention is to provide a novel and improved apparatus of the general character referred to which is not affected by the specific gravity of the oil contained in the sample fluid being tested and that can quickly and accurately determine the net oil content of oil well production fluid tested and analyzed without regard to the specific gravity of the oil therein.

Still another object and feature of my invention is to provide a novel apparatus of the general character referred to above that is extremely easy and economical to make and that is highly dependable and durable in operation.

It is an object of the invention to provide an apparatus of the character referred to above the mechanical parts of which include three valves and a valve operator to intermittently simultaneously operate the valves between opened and closed positions.

Yet another object and feature of my invention is to provide an apparatus of the general character referred to that includes an elongate vertical test pipe connected with and extending between a pair of normally closed valves and defining an elongate vertical test chamber, a flow pipe through which production fluid normally flows and in which a normally open valve is engaged, and valve actuator means to selectively open the normally closed valves and to close the normally open valve to bypass production fluid flowing through the flow pipe into and through the test pipe to fill the chamber with a sample of production fluid to be analyzed.

A further object and feature of my invention is to provide an apparatus of the character referred to including a flow meter in the flow pipe to read the flow rate of production fluid flowing therethrough and to transmit a corresponding flow rate signal; and, devices at the test pipe to read the pressure, temperature, weight and capacitance of a sample of production fluid in the test chamber and to transmit corresponding pressure, temperature, weight and capacitance signals.

Finally, it is an object and feature of my invention to provide an apparatus of the general character referred to above that includes a computer including an input section or means receiving and converting the pressure, temperature, weight and capacitance signals transmitted by the apparatus into corresponding feedback data, a memory section or means in which previously established control data is stored, a control section or means to receive and process feedback and control data received thereby from the input and memory means; and, an output section or means that translates and presents processed data and information for use.

The foregoing and other objects and features of my invention will be apparent and will be fully understood from the following detailed description of one typical preferred form and embodiment of my invention throughout which description reference is made to the accompanying drawings.

DETAILED DESCRIPTION OF THE INVENTION

Figure 1:
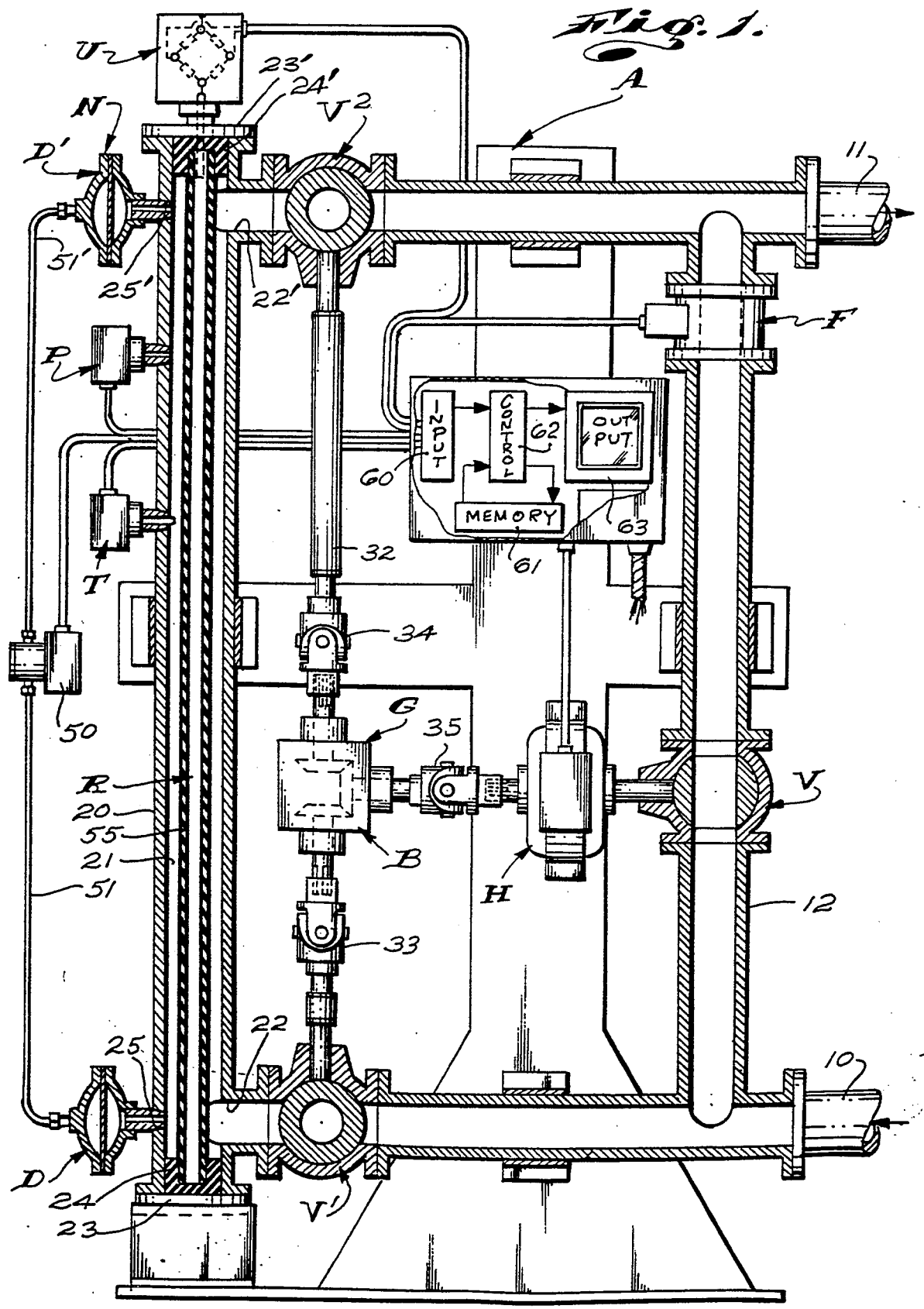
FIG. 1 is an elevational view of my new apparatus.

The apparatus A, shown in the drawing, is engaged between and connected with related outlet and inlet ends of upstream and downstream sections 10 and 11 of a production pipeline through which oil well production fluid produced by a well being monitored by the apparatus A flows at a normal rate and under normal pressure.

In practice, the pipe sections 10 and 11 can be parts of a valve controlled manifold system that is connected with and handles the production from a plurality of oil wells that are monitored by the apparatus and that is automatically operated to sequentially and intermittently conduct the production fluid from each of those oil wells into and from the apparatus, as desired and as circumstances require.

Since the novelty and spirit of this invention is in no way altered or affected by the number of wells it might be used to monitor or by the particular means by which the production fluid(s) from one or more oil wells might be conducted to and from it, I have elected not to unduly burden this disclosure with illustration and/or description of any one particular structure or means to handle inflowing and outflowing production fluid, other than to show the production pipeline sections 10 and 11 noted above.

The apparatus A first includes an elongate flow pipe 12 extending between and connected with the production pipeline sections 10 and 11 and through which oil well production fluid normally flows.

The flow pipe 12 has a normally open flow control valve V engaged therein. The valve V is selectively closed and opened to stop and start the flow of production fluid through the pipe 12, as will here and after be described.

In practice, a flow meter F can be and is preferably engaged in the flow pipe 12, downstream from the valve V. The flow meter F reads the rate of flow of production fluid through the pipe and transmits a corresponding flow rate signal.

In practice, the flow meter F is preferably one of those types of flow meters that has no moving parts and that is trouble-free and maintenance-free when used in the harsh environments (oil fields) in which the apparatus A is used. One type of flow meters that I have advantageously employed is a magnetic inductance type flow meter.

The apparatus A next includes an elongate vertically extending test pipe 20 with a lower inlet or upstream end portion and an upper outlet or downstream end portion. The pipe 20 defines an elongate, vertical, cylindrical in cross-section, test chamber 21.

The lower end portion of the pipe 20 has an inlet port 22 connected with the downstream side of a normally closed inlet valve V1. The other or upstream side of the valve V1 is suitably connected with the downstream end of the upstream section 10 of the production pipeline.

The lower end of the pipe 20 and the chamber 21 are closed by a suitable closure structure 23 that includes a lower rod support for insulator 24 of dielectric material. The structure 23 preferably includes a mounting flange on the pipe and a plate suitably fastened to the flange. The plate carries the rod support or insulator 24.

The lower end of the pipe 20 next and finally includes a port 25 that communicates with the lower end of the chamber 21 and in and through which a part of a fluid pressure sensing device D extends. The device D is preferably mounted on and carried by the pipe at the exterior thereof.

The upper end portion of the pipe 20 is similar to the lower end portion thereof and, as shown, has an inlet port 22' suitably connected with the upstream side of a normally closed outlet valve V2. The other or downstream side of the valve V2 is suitably connected with the upstream end of the downstream section 11 of the production pipeline.

The upper end of the pipe 20 and the chamber 21 are closed by a suitable closure structure 23', similar to the closure structure 23, and that includes an upper rod support or insulator 24' of dielectric material.

The upper end portion of the pipe 20, like the lower end portion thereof, includes a port 25' that communicates with the upper end of the chamber 21 and through which a part of a fluid pressure sensing device D', similar to the device D, is engaged. The device D', like the device D, is shown mounted at the exterior of the pipe 20.

The apparatus next includes a valve actuating means G that operates to simultaneously close the valve V and open the valves V1 and V2 to shut off the flow of production fluid through the pipe 12 and establish flow of that fluid through the pipe 20, to fill the chamber 21 with the fluid and to thereafter simultaneously open the valve V and close the valves V1 and V2 to trap a fluid sample in the chamber 21, without stopping or interrupting normal flow of production fluid in and through the pipeline with which the apparatus is connected.

The fluid filling and trapped in the chamber 21 in the manner set forth above, establishes a fluid sample of predetermined vertical and volumetric extent and that is under the normal or working pressure of the production fluid flowing through the pipeline is under.

It is to be noted that each time the several valves are operated in the manner set forth above, a previously tested fluid sample in the chamber 21 is displaced or moved downstream therefrom and is replaced by a new yet-to-be-tested fluid sample.

In practice, the several valves V, V1 and V2 are preferably alike. In the case illustrated, they are ball valves with operating stems accessible at their exteriors and that are actuated between open and close positions by rotation of the stems through 90°. The valves V1 and V2 are in vertical spaced relationship from each other and are arranged with their stems in axially aligned opposing relationship with each other. The valve V is laterally spaced from the center line along which the stems of the valves V1 and V2 extend and is arranged with its stem projecting toward the noted center line and on an axis perpendicular to it.

The valve actuating means G that I prefer to employ includes a right angle gear box B with an input shaft opposing and concentric with the stem of the valve V and with an output shaft axially aligned with and having lower and upper ends opposing the stems of the valves V1 and V2 and which are drivingly connected therewith by drive shafts 31 and 32. The drive shafts 31 and 32 are preferably provided with Universal joints 33 and 34, having splined coupler parts and that serves to compensate for misalignment and for thermal expansion and contraction of the parts of the apparatus related to them.

The valve actuating means G next includes a prime mover or drive motor H with a drive shaft with opposite ends projecting toward and aligned with the stem of the valve V and the input shaft of the gear box B. The motor H is shown mounted to a part of a frame for the apparatus and can be connected with its related valve stem and gear box input shaft by intermediate shafts or, as shown, the end of the drive shaft related to the stem of the valve V can be directly connected to that valve stem and the end of the drive shaft related to the input shaft of the gear box can be connected thereto by means of a suitable Universal joint 35 (with a splined coupling part).

The motor H can be an electric, hydraulic or pneumatic motor as desired or as circumstances require and is selectively operated to turn 90° and to thereby effect simultaneous actuation of the valves V, V1 and V2, between their opened and closed positions as required during normal and intended operation and use of the apparatus A.

The apparatus A next includes pressure and temperature sensing devices P and T suitably mounted on the exterior of the pipe 20 and having parts projecting through related ports formed in the pipe 20 and into the chamber 21. The devices P and T operate to sense the pressure and the temperature of the fluid sample in the chamber and to transmit corresponding pressure and temperature signals. The devices P and T can be any one of those several different kinds of standard pressure and temperature sensing devices one might elect to use when practicing my invention.

The above-noted pressure sensing devices D and D' at the upper and lower ends of the pipe 20 are parts of a density sensing means N that operates to measure the weight or density of the fluid sample and that transmit a corresponding density signal.

The devices D and D' can vary widely in form and are shown as simple diaphragm structures with pressure input sides exposed to the fluid sample within the chamber 21 and pressure output sides exposed to a suitable force transmitting fluid medium, such as hydraulic oil. The force output sides of the devices D and D' are connected with a comparator and translator unit 50 by means of capillary tubes 51 and 51', as clearly shown in the drawing. The unit 50 operates to compare the pressures sensed by the devices D and D' and to transmit the desired and corresponding density signal.

The device A next includes an elongate vertically extending electrode rod R with an outer jacket 55 of insulating material. The jacketed rod is positioned centrally within the test pipe 20 in uniform spaced relationship with the wall of the pipe 20 and to extend centrally throughout the longitudinal extent of the chamber 21. The lower end of the rod R is securely held and supported in and by the insulator 24 at the bottom of the pipe and chamber 21 and the upper end thereof is securely held and supported in and by the insulator 24' at the top of the pipe and chamber.

The rod R and pipe 20 are, in effect, the spaced electrodes of a capacitor structure and the fluid sample in the chamber is the dielectric of that capacitor structure. Accordingly, the pipe 20, rod R and fluid sample establish an effective electrical capacitor.

The jacket 55 about the rod R prevents the sample short circuiting between the rod and the pipe 20. Its dielectric properties are accounted for when the dielectric constant of the sample is determined.

The rod R and test pipe 20 of the noted capacitor structure are connected in and with a suitable comparator circuit, such as a bridge circuit, of a transmitter unit U that is shown conveniently mounted atop the closure structure 23' at the upper end of the pipe 20. A conductor to connect the unit U to the rod R can be extended through the closure structure 23', between the unit U and rod R, as illustrated in dotted lines. A high frequency AC voltage is applied to the bridge in the unit U and the bridge operates to measure the capacitance of the fluid sample and to emit or transmit a corresponding capacitance electrical signal.

It is to be noted that the dielectric fluid sample extends throughout the longitudinal extent of the chamber 21 and is deposited dimensionally uniformly about and between the opposing surfaces of the rod R and pipe 20. Accordingly, the resistance afforded thereby and read by the unit U is the average or mean resistance afforded by the whole of the sample. Accordingly, if the gas, water and oil fractions of the sample should separate, settle or otherwise become unevenly distributed throughout the chamber and about the rod and the pipe, a reading of the resistance or capacitance which is the average or mean resistance or capacitance afforded by the whole of the sample is attained.

It is believed apparent that any one of numerous different comparator circuits or bridge circuits that are known to exist can be utilized in practicing my invention.

The flow rate, pressure, temperature, density and capacitance signals transmitted by the flow meter F, means P, T, N and by the unit U, which signals will hereinafter be referred to as feedback signals, are suitably translated into corresponding digital or numerical data and, together with earlier acquired base data pertaining to the production fluid being tested, can be processed or used to calculate the net oil content and the net content of the water and gas in the fluid sample. If the data is numerically or mathematically calculated, considerable skill and time must be expended to attain the desired results. On the other hand, if the data is computed digitally, utilizing appropriate computer hardware and software, the desired information and/or answers can be attained quickly. For example, the data can be processed and the desired information can be presented in a matter of minutes rather than hours. Also, when the data is computed by means of an appropriate computer, the information and answers and all or any part of the data utilized to gain that information and to reach those answers can be transmitted by telephone service to a remote computer where the data and information can be recorded and put to use, by means of a modem.

In another use of my new apparatus, the transmitted feedback signals are stored in a retrievable form by means of or in a simple recording device that can be accessed by telephone. When it is timely or desired to record and/or process the stored signals or data, the recording device is accessed, by telephone, and the data is entered into a central computer and thereafter processed. In accordance with the foregoing, it will be apparent that large numbers of my apparatus, each serving a number of wells and spaced throughout large geographical areas can be monitored and managed at a single or central monitoring station.

In accordance with the above, though I do not make any claim to any particular computer hardware and computer software, such hardware and software are important collateral or support means and/or equipment used in conjunction with my apparatus to utilize its full useful potentials and to most effectively and efficiently realize all that it offers.

In the drawing, I have diagrammatically illustrated the basic components of a computer as might be used in conjunction with my apparatus. The computer includes an input means 60 which receives the several noted feedback signals from the apparatus and converts them into digital form; a memory means 61 in which previously obtained and/or prepared base or reference data is stored; a control means 62 that compares and processes data received from the input and memory means; and, an output section 63 that converts the data processed by the control means and presents it in readable and useable form.

To utilize and calculate the data obtained and provided by my apparatus and to obtain the information and/or answers sought, the following set of basic equations are used:

$$Qg = Vg * Fg * Ap$$

Where:
QG = Volumetric flow rate of gas, $Ft^3/sec$
Vg = Velocity of gas, Ft/sec
Fg = Fraction of gas in pipeline, dimensionless
Ap = Cross sectional area of pipe, $Ft^2$ $$Qo = Vl * Fo * Ap$$

Where:
Qo = Volumetric flow rate of oil, $Ft^3/sec$
Vl = Velocity of liquid, Ft/sec
Fo = Fraction of oil in fluid stream, dimensionless
Ap = Cross sectional area of pipe, $Ft^2$ $$Qw = Vl * Fw * Ap$$

Where:
Qw = Volumetric flow rate of water, $Ft^3/sec$
Fw = Fraction of water in fluid stream, dimensionless
Vl = Velocity of liquid, Ft/sec
Ap = Cross sectional area of pipe, $Ft^2$ Once the volumetric flow rates are established through the pipeline by means of the meter F, the volumes of gas and liquid, at standard conditions, are calculated using fluid property correlations and pressure and temperature measurements established by the devices P and T. These corrected volumetric rates are then integrated over the time length of the test to give the final test results.

The fractions of oil, water, and gas are related to each other by three simultaneous, linear equations. The three equations are:

$$Fo + Fw + Fg = 1 \qquad (1)$$

$$FoRhoo + FwRhow + FgRhog = Rhos \qquad (2)$$

$$FoEo + FwEw + FgEg = Es \qquad (3)$$

Where:
Fo = Fraction of oil (dimensionless)
Fw = Fraction of water (dimensionless)
Fg = Fraction of gas (dimensionless)
Rhoo = Density of oil, $lbs/in^3$
Rhow = Density of water, $lbs/in^3$
Rhog = Density of gas, $lbs/in^3$
Rhos = Density of sample, $lbs/in^3$
Eo = Dielectric constant of oil (dimensionless)
Ew = Dielectric constant of water (dimensionless)
Eg = Dielectric constant of gas (dimensionless)
Es = Dielectric constant of sample (dimensionless)

The density of the liquid sample is calculated by measuring the delta pressure between the pressures sensed by the vertically spaced devices D and D' or the means N. The basic equation for determining the density of the samples is:

$$Rhos = Rhof - Pd/Hc$$

Where:
Rhos = Density of sample, $lbs/in^3$
Rhof = Density of isolation diaphragm fill fluid, $lbs/in^3$
Pd = Delta pressure, $lbs/in^2$
Hc = Height between isolation diaphragms, inches The dielectric constant of the sample is determined by measuring the capacitance of the liquid sample in the chamber 21 and using the known dimensions of the chamber to calculate the dielectric constant. The basic equation is:

$$Es = (C * \ln(B/A) * k) / (2 * Pi * L)$$

Where:
- Es = Dielectric constant of sample, dimensionless
- C = Capacitance of sample, pF
- B = Radius of outer cylinder, Ft
- A = Radius of inner cylinder, Ft
- K = Scaling constant
- L = Length of cylinder, Ft The values of the dielectric constants and densities of the oil, water and gas are calculated from properties equations relating these values to temperature pressure.

It will be apparent that through use of my apparatus and related use of the several measurements made thereby in carrying out the above equations, the net content of oil, as well as the net content of water and/or gas, in the production fluid flowing from an oil well can be rapidly and accurately determined without regard to the differential between the densities or specific gravities of the oil and the water; without the need to separate and extract samples of the oil, gas and/or water; and, without the need to perform any special work on the sample of production fluid that is temporarily isolated from the main flow of production fluid being tested.

It will also be apparent that the apparatus that I provide is made of a small number of easy and economical to make, assemble and maintain parts and is sufficiently rugged and durable to withstand the environments in which it is likely to be used, for extended periods, without adverse effects.

Having described my invention, I do not wish to be limited to the specific details herein set forth but wish to reserve to myself any modifications and/or variations that might appear to those skilled in the art and which fall within the scope of the following claims.

Having described my invention, I claim:

1. An apparatus for the acquisition of data for use in calculating the net content of gas, oil and water in oil well production fluid flowing through a pipeline and compromising; an elongate, cylindrical, vertical test pipe defining a chamber of uniform cylindrical cross-section and of predetermined volumetric and vertical extent and connected with related upstream and downstream sections of the pipeline, an elongate flow pipe connected with and between upstream and downstream sections of the pipeline, valve means normally directing production fluid flowing through the pipeline through the flow pipe and selectively operated to intermittently redirect the flow of fluid through the test pipe and to releasably capture and statically hold fluid samples in the chamber, a flow rate indicating device connected with the flow pipe to acquire flow rate data of the fluid flowing therethrough, a temperature sensing device communicating with the chamber to acquire temperature data of fluid samples therein, a pressure sensing device communicating with the chamber to acquire pressure data of fluid samples therein, a density measuring means communicating with the chamber to measure and compare the pressures on fluid samples in the chamber at vertical spaced positions within the chamber and to acquire the density data of the samples, and, capacitance measuring means to measure the capacitance of fluid samples in the chamber and to acquire capacitance data; said capacitance measuring means includes an elongate electrode rod concentric with the test pipe and extending longitudinally through the chamber and fluid samples therein and in uniform spaced relationship from the test pipe; a jacket of dielectric insulating material about the rod; and, a comparator circuit connected with and between the electrode rod and the test pipe to measure a current conducted therebetween into and flowing through fluid samples in the chamber; said valve means includes a normally open flow valve in the flow pipe, a normally close inlet valve at an upstream end of the test pipe and connected with an upstream section of the pipeline and a normally closed outlet valve at a downstream end of the test pipe and connected with a downstream section of the pipeline; and valve actuating means to simultaneously close the flow valve and open the inlet and outlet valves to redirect fluid flowing through the flow pipe through the test pipe to fill the test pipe with the fluid flowing through the pipeline and to simultaneously reopen the flow valve and reclose the inlet and outlet valves to capture and statically hold a fluid sample in the chamber defined by the test pipe; said valves have rotating operating stems and said actuating means includes a motor and gear box with rotating shafts drivingly coupled with the valve stems, the inlet and outlet valves are arranged with their stems in axially aligned opposing spaced relationship from each other and the stem of the flow valve is spaced radially from and on an axis normal to the axis on which the stems of the inlet and outlet valves occur, the gear box has an output shaft with opposite ends aligned and drivingly connected with the stems of the inlet and outlet valves and an input shaft aligned with and in spaced relationship with the stem of the flow valves, said motor is positioned between and is drivingly connected with the input shaft of the gear box and the stem of the flow valve.

* * * * *